(12) United States Patent
Williams

(10) Patent No.: US 6,877,982 B2
(45) Date of Patent: *Apr. 12, 2005

(54) MANDIBULAR AND MAXILLARY ARCH EXPANDER HAVING POLYGONAL OR OVOID ROD AND TUBE EXPANDING ELEMENTS

(76) Inventor: Michael O. Williams, 58 Shoreline La., Gulfport, MS (US) 39053

( * ) Notice: Subject to any disclaimer, the term of this patent is extended or adjusted under 35 U.S.C. 154(b) by 121 days.

This patent is subject to a terminal disclaimer.

(21) Appl. No.: 10/186,604

(22) Filed: Jul. 2, 2002

(65) Prior Publication Data

US 2002/0172909 A1 Nov. 21, 2002

Related U.S. Application Data (63) Continuation-in-part of application No. 09/598,766, filed on Jun. 22, 2000, now Pat. No. 6,402,510, which is a continuation-in-part of application No. 09/406,426, filed on Sep. 27, 1999, now Pat. No. 6,241,517, which is a continuation-in-part of application No. 09/143,071, filed on Aug. 28, 1998, now Pat. No. 6,036,488, which is a continuation-in-part of application No. 09/065,344, filed on Apr. 23, 1998, now Pat. No. 5,919,042.

(51) Int. Cl.$^7$ .............................................. A61C 3/00
(52) U.S. Cl. ................................ 433/19; 433/7; 433/18
(58) Field of Search .............................. 433/7, 19, 18, 433/21, 22, 24

(56) References Cited

U.S. PATENT DOCUMENTS

| 3,525,153 A | 8/1970 | Gerber |
| 3,798,773 A | 3/1974 | Northcutt |
| 4,184,254 A | 1/1980 | Kraus |

(Continued)

FOREIGN PATENT DOCUMENTS

DE 29619489 6/1997

OTHER PUBLICATIONS

"Introducing the RMO Clark Trombone and Lingual Arch Developer", 1998.*

(Continued)

*Primary Examiner*—John J Wilson
(74) *Attorney, Agent, or Firm*—Paul M. Denk (57) ABSTRACT

An orthodontic appliance for expanding the mandibular or maxillary arch comprises a first forward orthodontic band; a second forward orthodontic band; a first spring-loaded rod and tube assembly between said first and second forward orthodontic bands; a first rear orthodontic band and a second rear orthodontic band; a second spring-loaded rod and tube assembly connecting said first forward and first rear orthodontic bands; and a third spring-loaded rod and tube assembly connecting said second forward and second rear orthodontic bands. Where both a maxillary and mandibular arch expander are used, they can be connected by a Herbst-type telescoping connector. The telescoping assembly has a first end connected to one of said forward and rear bands of said mandibular arch expander and a second end connected to the other of said forward and rear bands of said maxillary arch expander. The telescoping assembly includes a tube assembly and a rod slidably received in the tube assembly. In each of the various tube and rod assemblies (i.e. of the maxillary arch expander, the mandibular arch expander, and of the Herbst-type appliance), the tube of rod and tube assemblies defines a channel which slidably receives the rod of the rod and tube assemblies. The tube and rod have complementary cross-sectional shapes; the cross-sectional shape being polygonal or ovoid. The cross-sectional shape, for example, can be square, a circle truncated on one or two sides, or round.

11 Claims, 7 Drawing Sheets

U.S. PATENT DOCUMENTS

| | | |
|---|---|---|
| 4,245,986 A | 1/1981 | Andrews |
| 4,354,834 A | 10/1982 | Wilson |
| 4,373,913 A | 2/1983 | McAndrew |
| 4,384,851 A | 5/1983 | McAndrews |
| 4,424,032 A | 1/1984 | Howe |
| 4,433,956 A | 2/1984 | Witzig |
| 4,462,800 A | 7/1984 | Jones |
| 4,472,139 A | 9/1984 | Rosenberg |
| 4,482,318 A | 11/1984 | Forster |
| 4,619,609 A | 10/1986 | Clark |
| 4,671,767 A | 6/1987 | Blechman et al. |
| 4,723,910 A | 2/1988 | Keller |
| 4,795,342 A | 1/1989 | Jones |
| 5,064,370 A | 11/1991 | Jones |
| 5,066,226 A | 11/1991 | Summer |
| 5,266,028 A | 11/1993 | Adkisson |
| 5,352,116 A | 10/1994 | West |
| 5,443,384 A | 8/1995 | Franseen et al. |
| 5,505,616 A | 4/1996 | Harwell |
| 5,562,445 A | 10/1996 | DeVincenzo et al. |
| 5,645,422 A | 7/1997 | Williams |
| 5,711,667 A * | 1/1998 | Vogt ............................. 433/19 |
| 5,769,631 A | 6/1998 | Williams |
| 5,919,042 A | 7/1999 | Williams |
| 6,036,488 A | 3/2000 | Williams |
| 6,241,517 B1 | 6/2001 | Williams |
| 6,491,519 B1 * | 12/2002 | Clark et al. ................... 433/18 |

OTHER PUBLICATIONS

"Chapter 14—The Herbst Appliance"—Orthodonic & Orthopedic Treatment in the Mixed Dentition—By•McNamara & Brudon—Brudon—Needem Press—Nov., 1993.

Maxillary Expander Using Light, Continuous Force and Autoblocking, M. Ali Darendeliler, DDS, MSD and Carlo Lorenzon, DMD—JCO/Apr. 1996.

* cited by examiner

MANDIBULAR AND MAXILLARY ARCH EXPANDER HAVING POLYGONAL OR OVOID ROD AND TUBE EXPANDING ELEMENTS

CROSS-REFERENCE TO RELATED APPLICATIONS

This application is a continuation-in-part of application Ser. No. 09/598,766 now U.S. Pat. No. 6,402,510 filed Jun. 22, 2000 and entitled "Buccal Tipping-Resistant Mandublar And Maxillary Arch Expander," which is a continuation-in-part of application Ser. No. 09/406,426 filed Sep. 27, 1999, now U.S. Pat. No. 6,241,517 entitled "Mandibular And Maxillary Arch Expander," which is a continuation-in-part of application Ser. No. 09/143,071 filed Aug. 28, 1998, now U.S. Pat. No. 6,036,488, entitled "Pivotal Mounting Boss For Mandibular And Maxillary Arch Expander And Jaw Repositioner", which, in turn, is a continuation-in-part of application Ser. No. 09/065,344 filed Apr. 23, 1998, now U.S. Pat. No. 5,919,042, entitled "Mandibular And Maxillary Arch Expander And Jaw Repositioner", all of which are incorporated herein by reference. The invention is further related to the inventions shown and described in U.S. Pat. No. 5,769,631, entitled Orthodontic Device, which is a continuation-in-part of U.S. Pat. No. 5,645,422 entitled Mandibular And Maxillary Arch Expander, both of which are also incorporated herein by reference.

STATEMENT REGARDING FEDERALLY SPONSORED RESEARCH OR DEVELOPMENT

Not Applicable.

BACKGROUND OF THE INVENTION

This invention relates generally to orthodontic devices and, in particular, to an improved jaw expander to widen a patient's jaw.

Orthodontists treating children often need to gain space in a child's mouth for unerupted mandibular incisors and to increase intercanine distance for narrow archforms, as well as to distilize mandibular first molars so that a total increase of archlength is available in the lower dental arch from first molar to first molar. Furthermore, the orthodontist may want to expand the palate correspondingly.

Mandibular and maxillary arch expanders are known in the art to expand and lengthen the mandibular and maxillary archlengths. The use of such arch expanders help avoid the need for tooth extraction of permanent teeth due to overcrowding. However, such mandibular arch expanders are rather bulky in design, impede tongue mobility, are uncomfortable to wear, and interfere with good oral hygiene. The devices must be substantial in design to resist torquing or leverage mechanics during chewing.

To facilitate corresponding enlargement of the maxillary and mandibular arches, telescoping mechanisms have been employed which encourage forward repositioning of the lower jaw as the patient closes into occlusion. Such devices are commonly referred to as Herbst appliances. Current Herbst appliances include a hollow tube and a rod which is telescopically received in the tube. The tube is connected to the maxillary arch expander and the rod is connected to the mandibular arch expander. Generally, the tube and rod are connected to a band or stainless steel crown by a pivoting connection. The pivot generally comprises a base casing which is soldered or welded to the band or crown and a screw that is inserted through an eye formed on the end of the hollow tube or rod. The screw threadedly engages the base casing and is tightened, leaving enough clearance for the eye to pivot about the screw. Often the orthodontist uses an arch wire connected between the two ends of the arch expander. In the past, to accommodate the arch wire, the orthodontist or technician first must attach a rectangular wire tube to the band or crown and then attach the base case on top of the rectangular tube. This arrangement has a relatively high profile caused by the stacking of the rectangular tube and base casing along with the increased solder mass.

BRIEF SUMMARY OF THE INVENTION

A new expansion complex is provided for a mandibular arch expander. The mandibular arch expander includes first and second forward orthodontic bands and a pair of rear orthodontic bands operatively connected to the forward orthodontic bands. The expansion complex includes an arm extending lingually from a lingual side of the first forward orthodontic band. An expander body or tube is rotationally mounted on the arm to rotate about the arm. A passage extends through the body, and the arm extends into a rear end of the passage. The body passage is internally threaded near the front of the body. An expansion rod is mounted to a lingual side of the second forward orthodontic band. The expansion rod is externally threaded at a rear end thereof to be threadedly received in the threaded portion of the body passage. The expansion rod has a bore extending forwardly from the rear end of the rod which receives the arm. The back end of the body passage can be counterbored to receive a coil spring which is journaled about the arm.

BRIEF DESCRIPTION OF THE SEVERAL VIEWS OF THE DRAWINGS

Corresponding reference numerals will be used throughout the several figures of the drawings.

DETAILED DESCRIPTION OF THE INVENTION

The following detailed description illustrates the invention by way of example and not by way of limitation. This description will clearly enable one skilled in the art to make and use the invention, and describes adaptations, and variations of the invention, including what I presently believe is the best mode of carrying out the invention.

Figure 1:
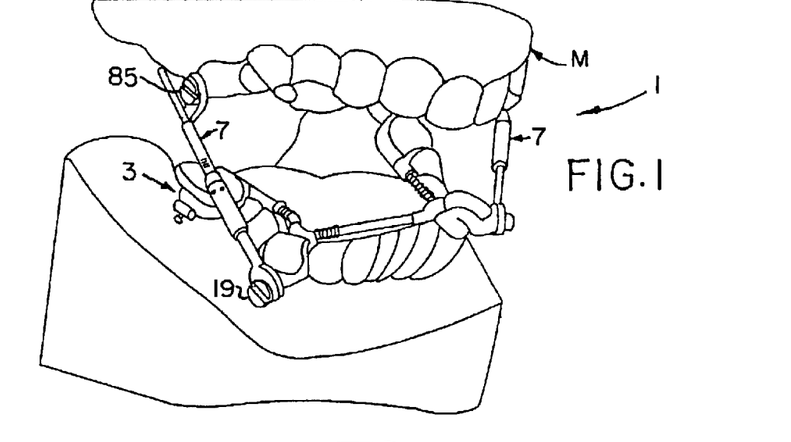
FIG. 1 is a perspective view of a mandibular arch expander and maxillary arch expander which are shown mounted in a mold and connected by a telescoping assembly.
Figure 1A:
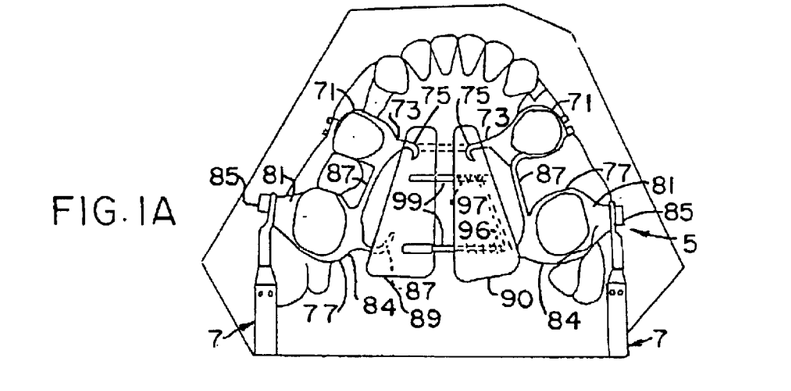
FIG. 1A is a bottom plan view of the maxillary arch expander mounted in the mold with the telescoping assembly mounted thereto.
Figure 1B:
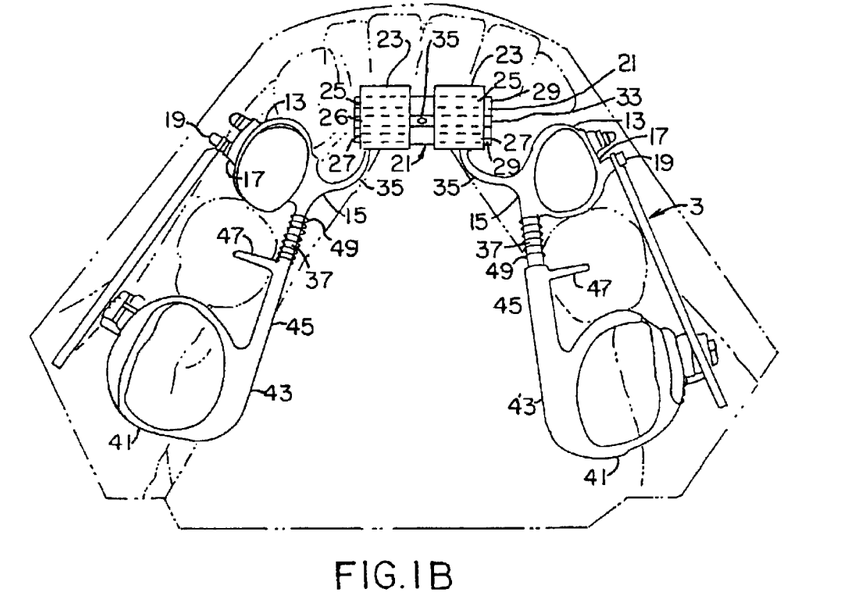
FIG. 1B is a top plan view of the mandibular arch expander mounted in the mold with the telescoping assembly mounted thereto.

Turning initially to FIGS. 1–1B, an orthodontic appliance 1 of the present invention is shown mounted in a mold M of a mouth. Although the appliance 1 is shown mounted in a mold, it will be appreciated that it is designed for use in a human mouth to increase the size of a child's mouth so that the child's permanent teeth will not be crowded when they erupt. This will reduce the need for extractions of permanent teeth. The appliance 1 includes a mandibular arch expander 3, a maxillary arch expander 5, and a pair of telescoping assemblies 7 which extend between and connect the mandibular and maxillary arch expanders 3 and 5, as described below.

The mandibular and maxillary arch expanders 3 and 5 are substantially the same as the arch expanders set forth in my above noted U.S. Pat. No. 5,645,422, which is incorporated herein by reference. The mandibular arch expander 3 (FIG. 1B) has a pair of spaced apart forward orthodontic bands 13 which are adapted to attach to the mandibular first primary molars. Bands 13 each have a boss 15 positioned on the lingual side of the bands and a boss 17 positioned on the buccal side of the bands. The buccal bosses 17 are adapted to receive screws 19 to connect the telescoping assemblies 7 to the mandibular arch expander 3, as will be discussed below. The respective bosses 15 and 17 are integrally formed on the respective bands to provide a substantial metallic body for the attachment of other elements to be described hereinafter. While the buccal bosses are shown attached to the outer sides of the bands, it is just as likely that these bosses may be intervened, on the side of the bands, with slight extensions, so as to locate the telescoping assemblies 7 a little more spaced, from the bands, as can be understood.

The bands 13 are interconnected by an expansion complex 21. The expansion complex 21 has a pair of metal blocks 23. The blocks 23 each have three bores 25, 26, and 27 formed laterally therethrough. The bores 25, 26, and 27 of the two blocks 23 are in substantial horizontal alignment. Aligning pins 29 extend through the outer bores 25 and 27. The respective aligning pins 29 are slightly undersized relative to the respective bores 25 and 27 so that the blocks 23 will slide relative to the pins 29. The middle bores 26 are threaded and receive a threaded screw 33. There is at least one hole 35 formed through the middle of screw 33 between the oppositely threaded ends. The hole 35 accommodates the insertion of a small tool to turn screw 33. It will be appreciated that threaded screw 33 has oppositely threaded ends. Therefore, when screw 33 is rotated in one direction, the blocks 23 are moved away from each other and when screw 33 is rotated in the opposite direction, the blocks 23 are drawn toward each other. The blocks 23 slide on the aligning pins 29 and the aligning pins serve to stabilize the expansion screw complex.

The blocks 23 are mounted to the lingual bosses 15 by curved arms 35 which extend between the bosses 15 and the block 23. The curved arms 35 can be of any appropriate length and curvature to suitably engage the patient's teeth. The mold M is made following conventional procedures and the arms 35 are fabricated to be the appropriate length and curvature. The arms 35 then are soldered to the appropriate boss 15 and to the expansion screw complex 21.

A rod 37 extends rearwardly from each of the lingual bosses 15. The rod 37 can be a small hollow tube, to reduce weight, or can be a solid rod. A stated above, the exact position on the respective bosses 15 where the rods 37 are attached and the angle at which the rod 37 extends from the bosses 15 depends upon the patient and the patient's needs. It will be appreciated that arms 35 and rods 37 can be one integral piece appropriately bent to form the arm and the rod, or the arm and rod can be separate pieces. To add to the convenience of the patient, it is also likely that the combined rod and tube assembly could be embedded in an acrylic, to add some comfort to the patient, particularly when, for example, the patient may rub his/her tongue against that combination, which may become abrasive. Hence, embedding it in a soft acrylic, adds protection against that, but will not detract from the functionality of the rod and hollow tube arrangement, as explained.

The mandibular arch expander 3 also has a pair of spaced apart rear orthodontic bands 41. The bands 41 generally are molar bands and, in use, are attached to the permanent first molars. Each band 41 has an integral boss 43 positioned on the lingual side of the bands. A hollow tube 45 extends forwardly from each boss 43. The hollow tubes 45 have an internal bore sized to accommodate the sliding insertion of the rods 37, as will be explained in detail below.

A pair of short wires 47 extends perpendicularly from the tubes 45. The respective short wires 47 extend buccally and serve as occlusal rests and are soldered on the respective tubes at a position corresponding to the lingual occlusal groove of the deciduous second molars bilaterally to provide extra support and stability to the tubes.

The forward pair of orthodontic bands 13 is connected to the rear pair of orthodontic bands 41 to promote molar distalization and added archlength development by a pair of spring-loaded rod and tube assemblies. Rods 37 are slidingly engaged in tubes 45. Coil springs 49 are positioned around rod 37 and fixed between bosses 15 and the end of the tube 45. The coil springs 49 are sized so they abut the ends of the tubes 45 and do not slide over the tubes 45. The respective coil springs 49, therefore, urge the forward bands 13 away from the rear bands 41 to increase palate length.

The coil springs 49 have a preset tension. The preset tension of the spring is selected by the orthodontist to effect the appropriate mesial distal archlength development in the bicuspid area.

Figure 1C:
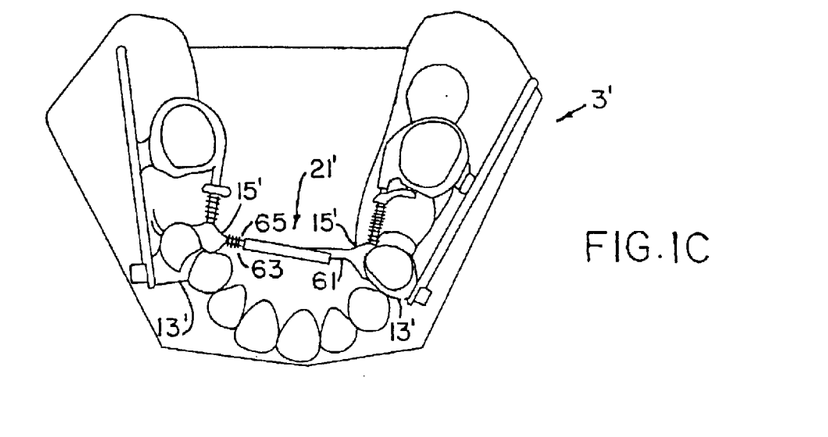
FIG. 1C is a top plan view similar to that of FIG. 1B, but with an alternative mandibular arch expander.

An alternative embodiment of the mandibular arch expander 3' of the present invention is shown in FIG. 1C. The mandibular arch expander 3' is substantially identical to the mandibular arch expander 3 shown in FIG. 1B. It varies, however, in the construction of the expansion complex 21'. The arch expander 3' includes spaced apart forward orthodontic bands 13' having lingual bosses 15'. The expansion complex 21' includes a hollow tube 61 extending from one boss 15' and a rod 63 extending from the other boss 15'. The angles at which the tube 61 and rod 63 extend from the respective bosses depend upon the shape of the patient's mouth. The rod 63 is slidingly engaged in the tube 61. A coil spring 65 is journaled around the rod 63 and fixed between the boss 15' and the end of the tube 61. The spring 65 is sized to engage the end of the tube 61 and not slip over the tube 61. Therefore, the spring 65 urges the forward bands 13' away from each other. The spring 65 has a predetermined force to be delivered between the molars to widen the anterior canine width.

The maxillary palatal expander 5 (FIG. 1A) has a pair of spaced apart forward orthodontic bands 71 which are adapted to attach to the maxillary molars. The each band 71 has a boss 73 positioned on the lingual side of the bands. The respective bosses are integrally formed on the respective bands. There is an integral curved member or hook 75 extending inwardly or lingually from the bosses 73.

A pair of spaced apart rear orthodontic bands 77 are positioned rearwardly of the forward bands 71. The bands 77 each have an integral lingual boss 79 and an integral buccal boss 81. The lingual bosses 79 have an integral curved member or hook 83. The buccal bosses 81 each have a screw hole to revive a screw 85 to connect the telescoping tube assemblies 7 to the maxillary arch expander 5.

The forward orthodontic bands 71 are connected to the rear orthodontic bands 77 by a rod 87. Furthermore, the hooks 75 and 83 are embedded in plastic plates 89 and 90. The respective plastic plates are molded to fit the patient's palate. Each plate, with the associated forward and rearward bands, comprises half of the expander 5. The halves of the expander 5 are biased away from each other to widen the maxillary arch. There is a substantially U-shaped rod 91 imbedded in plate 90. The rod 91 has legs which extend out from, and at substantially right angles to, the plastic plate 90. Coil springs 96 and 97 are journaled around the legs of the rod, respectively. A pair of short tubes 99 are embedded in the plate 89. The tubes 99 extend out of the palate plate 89 at substantially right angles to the palate plate. The tubes 99 are on complementary alignment with the legs of the U-shaped rod 91 and are slightly oversized so that the legs can slide into the tubes. The springs 96 and 97 abut the ends of the tubes 99 and exert tension force to urge the halves of the appliance apart. The appropriate tension can be exerted by selecting springs with the appropriate tension. The mandibular expander 3 of FIG. 1B can be modified to replace its expansion complex 21 with the plates 89 and 90 of FIG. A, and to include the structure associated with the plates 89 and 90.

To facilitate transverse development of the lower jaw relative to the upper jaw, the maxillary and mandibular arch expanders are interconnected by the telescoping Herbst-type assemblies 7, which are shown in detail in FIGS. 2-10. The two assemblies are identical and include a posterior tube 101, an anterior tube 103, and a rod 105 which extends through the two tubes 101 and 103. The posterior tube 101 includes a hollow body 107 which is open at both its front and back ends. The body 107 has an outer diameter which is substantially constant between its front and back ends. The back end 109 is externally threaded, as at 111. An arm 113 extends upwardly from the tube's body 107 at the front 115 of the body. The arm 113 has an eyelet 117 at its free end, the eyelet having a hole 119 therein. Intermediate its front and back ends, the posterior tube 101 includes a plurality of tick marks 121 which are used to indicate the amount of advancement of the anterior tube 103 over the posterior tube 101, as will be described below. The tick marks 121 are preferably separated by about one-millimeter.

Figures 2, 3, 4, 5, 6, 7, 8, 9, 10:
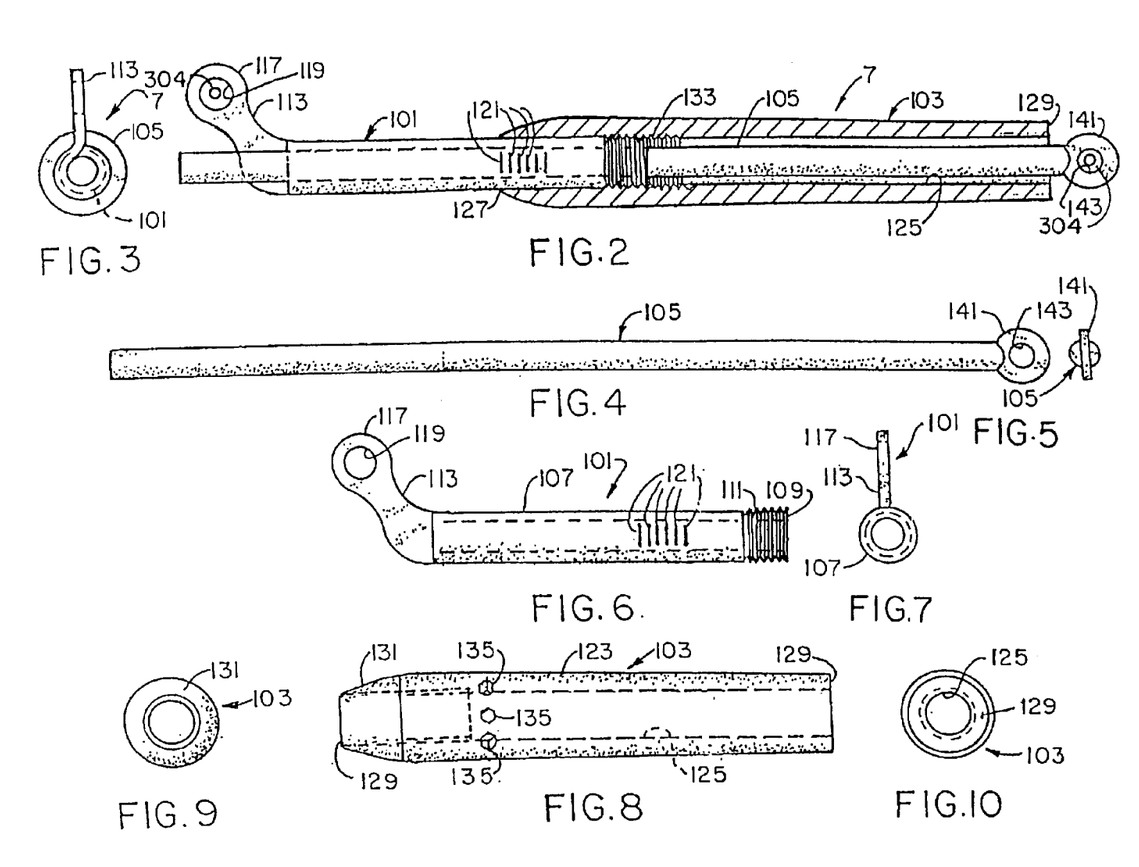
FIG. 2 is a side elevational view of the telescoping assembly, partially in cross-section.
FIG. 3 is a front plan view of the telescoping assembly.
FIG. 4 is a side elevational view of a rod of the telescoping assembly.
FIG. 5 is a front elevational view of the rod.
FIG. 6 is a side elevational view of a posterior tube of the telescoping assembly.
FIG. 7 is a rear elevational view of the posterior tube.
FIG. 8 is a side elevational view of an anterior tube of the telescoping assembly.
FIG. 9 is a front end elevational view of the anterior tube.
FIG. 10 is a back end elevational view of the anterior tube.

The anterior tube 103 includes a hollow body 123 defining a bore 125 therethrough. The tube 103 is open at both its back and front ends 127 and 129, respectively. The front end 127 of the tube tapers inwardly, as at 131 such that the very front of the tube 103 has a smaller outer diameter than the rest of the tube's body 123. As seen in FIGS. 8 and 10, the body 123 also tapers slightly from the back of the surface 131 to the back 129 of the body 123. The tube 123 is internally threaded at its front end, as at 133. The diameter of the bore 125 is slightly greater than the outer diameter of the anterior tube 101, and the threads 111 and 133 of the tubes 101 and 103, respectively, are machined or otherwise formed so that they will mate. Thus, the anterior and posterior tubes 101 and 103 are threadedly connected together. Notches or holes 135 are formed on the exterior of the posterior tube body 123. The notches 125 are adapted to receive a tool having a correspondingly shaped head. The tool can be used to rotate the posterior tube 103 relative to the anterior tube 101 when the appliance 1 is mounted in a patient's mouth.

The rod 105 is a generally straight rod. It has a generally constant diameter slightly greater than the inner diameter of the anterior tube 101, so that it may slide relative to the tube 101. At its back end, the rod 105 has an eyelet 141 having a hole 143.

The telescoping tube assemblies 7 are assembled by threadedly connecting the anterior and posterior tubes 101 and 103, and sliding the rod 105 into the tube assembly. The rod 105 is slid into the tube assembly such that its eyelet 141 will be at the opposite end of the assembly from the anterior tube eyelet 117.

As best seen in FIG. 1, the tube assemblies 7 extend between the forward bands 13 on the mandibular arch expander 3 and the rear bands 77 on the maxillary arch expander 5. The screws 85 of the maxillary arch expander pass through the eyelet's 117 of the anterior tubes 101 to pivotally connect the tube assembly to the maxillary arch expander. Similarly, the screws 19 of the mandibular arch expander 3 pass through the eyelets 141 of the rod 105 to connect the assembly 7 to the mandibular arch expander 3.

When initially inserted in a patient's mouth, the telescoping tube assemblies 7 are sized such that the back end 129 of the posterior tube 103 is in contact with the eyelet 141 of the rod 105 when the patient's mouth is shut. This will apply a forwardly directed pressure on the mandible. Thus, with all the components (i.e., the mandibular and maxillary arch expanders 3 and 5, and the telescoping tube assemblies 7 and 8) installed in a patient's mount, the appliance 1 will allow for transverse development, archlength development, palatal expansion and mandibular advancement, simultaneously without requiring patient compliance.

By rotating the tube 103 in one direction, the tube 103 will advance over the tube 101, to shorten the overall length of the tube assembly 7. Conversely, by rotating the tube 103 in a second direction, the tube 103 will be retracted relative to the anterior tube, to increase the overall length of the tube assembly. The extent of the movement of the tubes 101 and 103 relative to each other is measured by the tick marks 121. The interior threads 33 of the tube 103 and the tick marks 121 of the tube 101 are positioned on their respective tubes, such that when the tube 101 is threaded into the tube 103, the tick marks 121 will be exposed. By rotating the two tubes relative to each other, the number of tick marks exposed increases or decreases, depending on the direction of rotation, to indicate how far the tube assembly has been lengthened or shortened by the rotation of the tubes relative to each other. Thus, by reading the number of tick marks exposed, the practitioner can determine the amount of advancement that has occurred, as well as the overall length of the assembly 7.

Figure 1D:
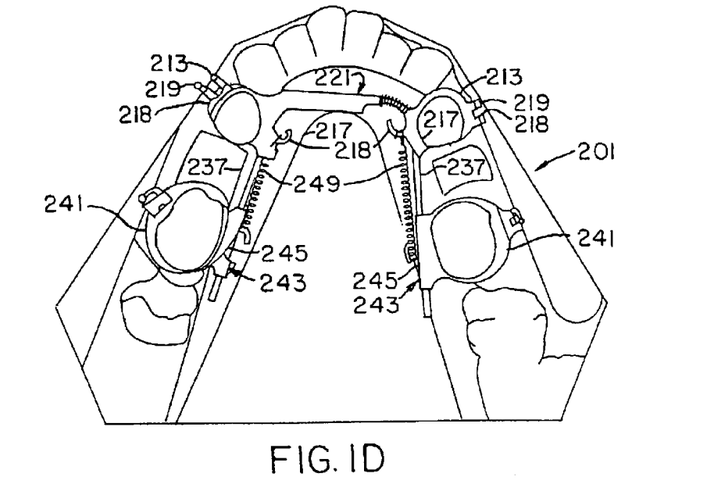
FIG. 1D is a top plan view of a mandibular molar space closer which can be used with the telescoping assembly.

A mandibular molar space closer 201 is shown in FIG. 1D. As can be seen, it is similar to the mandibular arch expander of FIG. 1C. The molar space closer 201 has a pair of spaced apart forward orthodontic bands 213 which are adapted to attach to the mandibular first primary molars. The bands 213 each have a boss 215 positioned on the lingual side of the bands and a boss 217 positioned on the buccal side of the bands. The buccal bosses 217 are adapted to receive screws 219 to connect the telescoping assemblies 7 to the mandibular arch expander 3. The respective bosses 215 and 217 are integrally formed on the respective bands to provide a substantial metallic body for the attachment of other elements to be described hereinafter. A hook 218 extends from the buccal boss 217 and points forwardly, toward the front of the patient's mouth.

The bands 213 are interconnected by an expansion complex 221. The expansion complex 221 which is identical to the expansion complex 21' of the mandibular arch expander 3'.

A rod 237 extends rearwardly from each of the lingual bosses 217. The rod 237 can be a small hollow tube, to reduce weight, or can be a solid rod. A stated above, the exact position on the respective bosses 217 where the rods 237 are attached and the angle at which the rod 237 extends from the bosses 217 depends upon the patient and the patient's needs.

The mandibular molar space closer 201 also has a pair of spaced apart rear orthodontic bands 241. The bands 241 generally are molar bands and, in use, are attached to the permanent first molars. Each band 241 has an integral boss 243 positioned on the lingual side of the bands. A hollow tube 245 extends along the lingual side of the band and through the boss 243. The hollow tubes 245 have an internal bore sized to accommodate the sliding insertion of the rods 237. The rods 237 sized such that they will pass through the tubes 245 to extend beyond the rear of the tubes 245.

The forward pair of orthodontic bands 213 are connected to the rear pair of orthodontic bands 241 to reduce the spacing between molars using a pair of spring-loaded rod and tube assemblies. Rods 237 are slidingly engaged in tubes 245, as noted. Coil springs 249 are connected to the rod 237 behind the rear molar band 241 and to the hooks 217. As seen, in this position, the springs 249 are in an expanded state. The respective coil springs 249, therefore, pull the bands 213 and 241 towards each other to decrease the spacing between molars. The coil springs 249 have a preset tension. The preset tension of the spring is selected by the orthodontist to effect the appropriate mesial distal archlength development in the bicuspid area.

Figure 11:
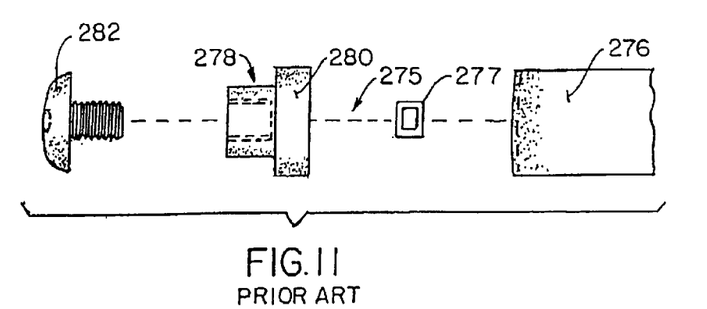
FIG. 11 is an exploded view of a prior art pivotal mounting boss assembly and an orthodontic band with a rectangular tube interposed to accommodate an arch wire.
Figure 12:
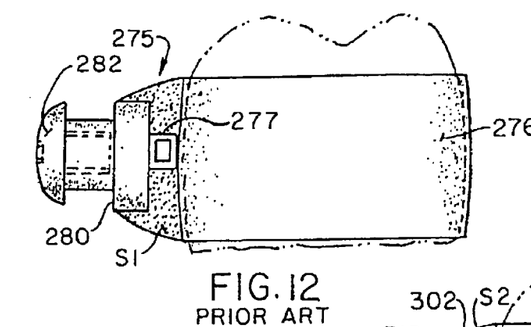
FIG. 12 is a perspective view of the prior art pivotal mounting boss assembly of FIG. 11 attached to an orthodontic band with a rectangular tube interposed to accommodate an arch wire.

A prior art mounting boss assembly gerry-rigged to accommodate an arch wire W is shown in detail in FIGS. 11 and 12 and indicated generally by reference numeral 275 shown in use with an orthodontic band 276. It will be appreciated that assembly 275 is described as attached to an orthodontic band but can be attached to a stainless steel crown as well Assembly 275 functions as the above described bosses attached to the orthodontic bands. However, assembly 275 is modified to allow the attachment of arch wires. The prior art assembly 275 includes a short segment of square tubing 277 which is attached to the band 276 by soldering, as at S1, for example. The square tubing is positioned on the orthodontic band for the attachment of an arch wire W, if needed. A mounting boss 278 including a base casing 280 and a screw 282 is then soldered on top of the square tubing. It will be appreciated by those skilled in the art that the prior art assembly 275 requires a substantial solder joint S1 to secure the elements which results in a high profile boss. Moreover, installation of the boss on the band requires addition time and costs.

Figure 13:
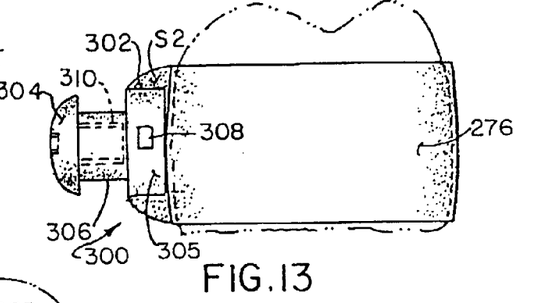
FIG. 13 is a perspective view of the improved pivotal mounting boss assembly of the present invention attached to an orthodontic band.
Figure 14:
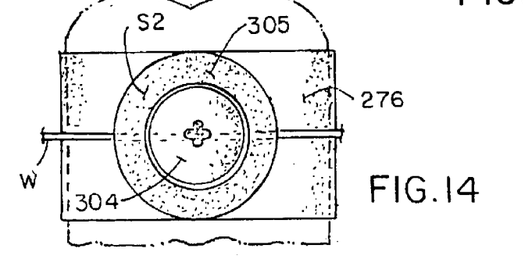
FIG. 14 is a top plan view of the improved pivotal mounting boss assembly.

An improved pivotal mounting boss is illustrated in FIG. 13 and shown in application in FIGS. 1, 1C and 2 is indicated generally by reference numeral 300. Mounting boss 300 includes a base casing 302 and a threaded screw 304. Base casing 302 includes a generally cylindrical base segment 305 and a concentric cylindrical body segment 306. Base segment 305 has an opening 308 formed therein. In the illustrated embodiment opening 308 is rectangular and is designed to accommodate a conventional arch wire W. See FIG. 14. The base segment 304 can be positioned on the orthodontic band 276 and soldered in place with solder S2. It will be appreciated that the opening 308 can be positioned at a predetermined angle as desired by the orthodontist for root angulation. It will be appreciated that less solder S2 is required to attach the mounting boss 300 to the orthodontic band resulting in less bulk and a lower profile arrangement than that shown in FIG. 12.

The body segment 306 includes an internally threaded bore 310 for the threaded engagement of screw 304 The screw 304 is inserted through the eyelet of the orthodontic device described above and tightened, leaving enough clearance so that the eyelet can rotate or pivot about the screw.

Figure 15:
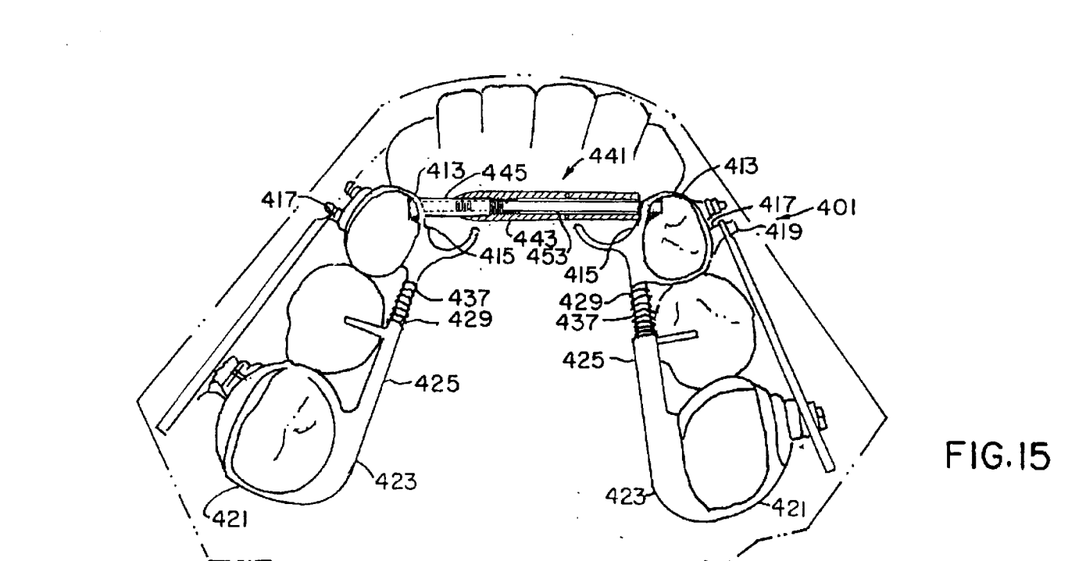
FIG. 15 is a top plan view, partly in cross-section, of an alternative mandibular arch expander using a telescoping assembly.

Another mandibular arch expander 401 is shown in FIG. 15. Although the expander 401 is shown embodied in a mandibular arch expander. It will be apparent that it can also be embodied in a maxillary arch expander. The expander 401 is substantially similar to the expander 3 of FIG. 1B. The mandibular arch expander 401 has a pair of spaced apart forward orthodontic bands 413 which are adapted to attach to the mandibular first primary molars. The bands 413 each have a boss 415 positioned on the lingual side of the bands and a boss 417 positioned on the buccal side of the bands. The buccal bosses 417 are adapted to receive screws 419 to connect the telescoping assemblies to the mandibular arch expander.

A rod 437 extends rearwardly from each of the lingual bosses 415. The rod 437 can be a small hollow tube, to reduce weight, or can be a solid rod. A stated above, the exact position on the respective bosses 415 where the rods 437 are attached and the angle at which the rod 437 extends from the bosses 415 depends upon the patient and the patient's needs.

The mandibular arch expander 401 also has a pair of spaced apart rear orthodontic bands 421. The bands 421 generally are molar bands and, in use, are attached to the permanent first molars. Each band 421 has an integral boss 423 positioned on the lingual side of the bands. A hollow tube 425 extends forwardly from each boss 423. The hollow tubes 425 have an internal bore sized to accommodate the sliding insertion of rods 437 which extend rearwardly from the forward orthodontic bands 413. Springs 429 are mounted on the rods 427 to apply a pressure to the forward orthodontic band, as discussed above. It will be appreciated that arms 429 and rods 437 can be one integral piece appropriately bent to form the arm and the rod, or the arm and rod can be separate pieces.

The difference between the mandibular arch expanders 3 and 401 lie in the expansion complexes of the two expanders. The expansion complex 441 uses an advancing sheath design which is similar to the sliding element 7 of FIGS. 2-10. The expander assembly is shown on an enlarged scale in FIG. 16. It includes a body 443 and a rod 445. The body 443 is hollow and defines a passageway 447 through the body. The passageway is open at its back end 449 and its front end 451. The body 403 is internally threaded, as at 452. The threads 453 are shown to be spaced rearwardly of the front end 451 of the passageway 447. However, the threads can extend throughout as much or as little of the body passageway as desired.

Figure 16:
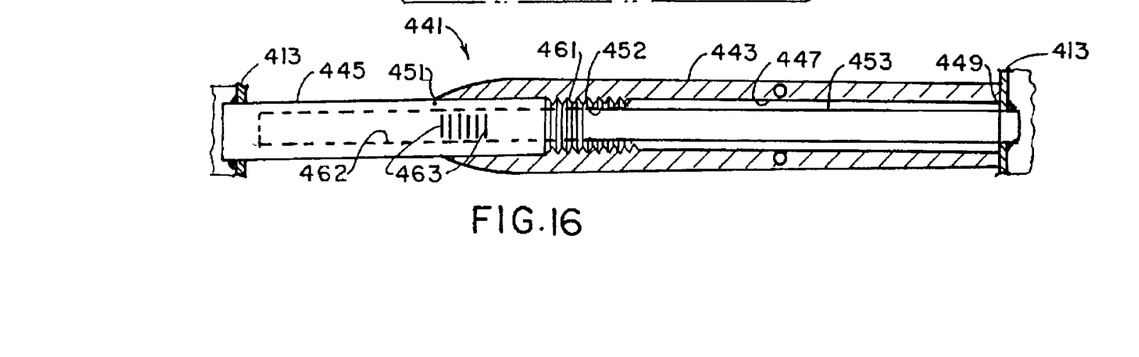
FIG. 16 is an enlarged cross-sectional view of the telescoping assembly of FIG. 15.

An arm 453 is received in the back end 449 of the passageway 447 and extends through the body 443 and out the front end 451 of the body 443. The arm 453 extends from the lingual boss 415 of one of the forward molar bands 413. The arm 453 and body boss 447 are sized so that the body 443 can rotate about the arm 453.

The rod 445 is sized to fit within the body passageway 447. A rear portion 461 of the rod 445 is externally threaded, so that the rod can be screwed into the body 403. At least a portion of the rod 445 is hollow, defining a bore 462 which extends forwardly from the back end of the rod 445. The bore 462 is sized to telescopically receive the forward end of the arm 453. A plurality of tick marks 463 are formed on the rod 445 forwardly of the threads. As with the assembly 7, the tick marks 463 enable the practitioner to know how far the rod 445 is extending from the body 403. The forward end 465 of the rod 445 is soldered, or otherwise fixed to, the lingual side of the other forward orthodontic band 413.

Thus, the rod 445 is effectively fixed to one of the forward orthodontic bands and the body 443 is effectively rotationally mounted to the other of the forward orthodontic bands. As seen in FIG. 15, the back end 449 of the body 443 is in abutting contact with the band 413 to which the arm 453 is mounted. Therefore, by rotating the body 443 relative to the rod 445, the overall length of the expansion complex can be selectively increased over time to increase the width of a patients jaw. Using the tick marks 463 on the rod 445, the dentist or technician can determine the overall length of the expansion complex, and can thus monitor the patient's progress.

Figure 17:
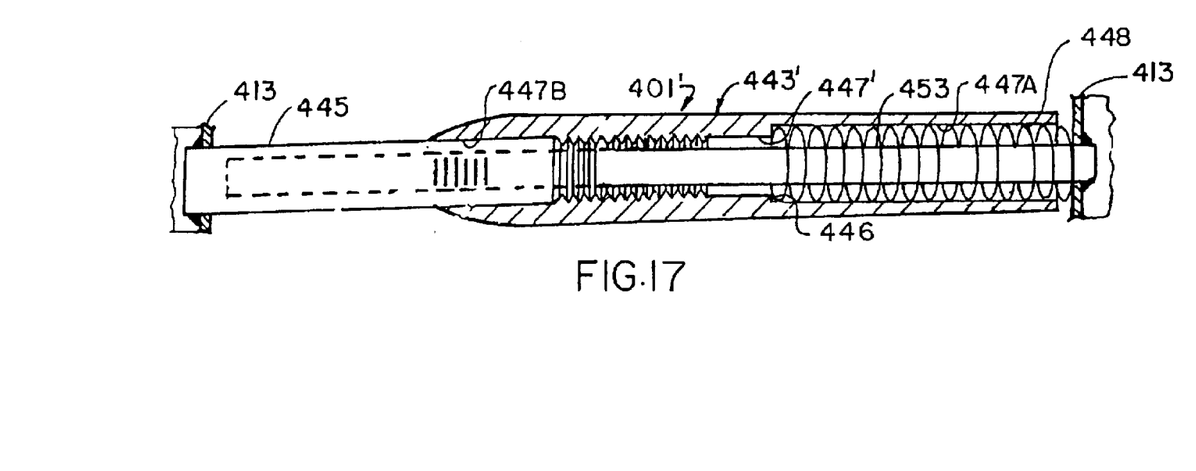
FIG. 17 is a cross-sectional view of the telescoping assembly of FIG. 16 wherein the telescoping assembly is provided with a coiled spring.

A modified expansion complex 401' is shown in FIG. 17. The expansion complex 401' is substantially identical to the expansion complex 401 of FIG. 15, and includes the rod 445 and arm 453. The difference is that the passage 447' of the body 443' is counterbored, as at 447A, to effectively produce a passage of two different diameters, the passage having a larger diameter in the back portion 447A than in the front portion 447B, with a shoulder 446 at the transition between the two sections. A coiled spring 448 is received in the counterbored portion 447A of the passage 447' and is coiled about the arm 453. The spring 448 is preferably a nickel-titanium spring and is sandwiched between the molar band 413 to which the arm 453 is mounted and the shoulder 446. The advantage of the spring 448 is that it will apply a constant pressure to the mandible to expand the mandible. Further, the expansion force comes from the spring, rather than from the back edge of the body 443. However, adjustments would still be made by rotating the body 443. The passage 447 in the body 443 (FIGS. 15 and 16) need not extend all the way through the body 443. The body could have a rear bore which accepts the arm 453 and a forward internally threaded bore which accepts the rod 445. This example is merely illustrative.

Figure 18:
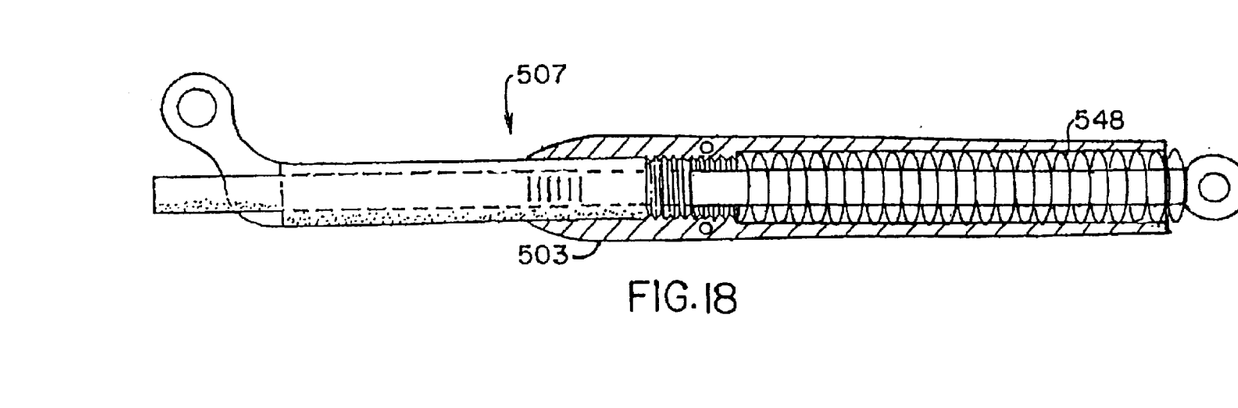
FIG. 18 is a cross-sectional view of a telescoping assembly similar to FIG. 2, but adapted to include a coiled spring

FIG. 18 shows a telescoping assembly 507 similar to the assembly 7 if FIG. 2. However, the assembly 507 has been modified to include a spring 548 in the body 503, similarly to the telescoping assembly 441 of FIG. 17.

Although the foregoing designs work well in most treatments, the inventor has determined that there can be some molar crown tipping in the transverse dimension analysis. To correct that problem, the inventor has developed modifications to the design that feature tubes having cylindrical outer configuration with an inner lumen that has flat sides. The rod which seats in the lumen has a complementary configuration. This design resists the turning or rotation of the rod within the tube which can result in molar crown tipping during treatment. The new designs are best illustrated in FIGS. 19–27.

Figure 19:
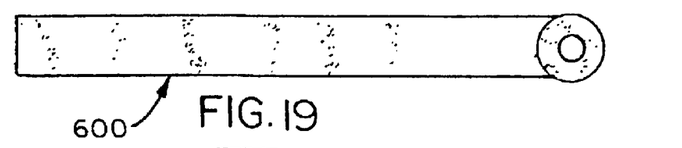
FIG. 19 is a side elevational view of an alternative embodiment of a rod of the telescoping assembly.
Figure 20:
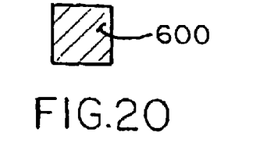
FIG. 20 is a front elevational view of the rod.
Figure 21:
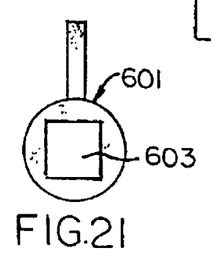
FIG. 21 is a rear elevational view of an alternative embodiment of the posterior tube.

FIGS. 19–21 illustrate one embodiment of the modified tube and rod indicated by reference numerals 600 and 601 respectively. As will be appreciated, the gross structure of the modified tube and rod are similar to those described above. However, as best seen in FIGS. 20 and 21, the rod 600 has a rectangular cross section. Tube 601 has a complementary rectangular bore 603, which is slightly oversized relative to tube 601 to allow the introduction of rod 600 into bore 603. As will be appreciated, the rectangular shapes of the bore and rod prevent the rod from turning or rotating within the tube to retard molar tipping in use.

Figure 22:
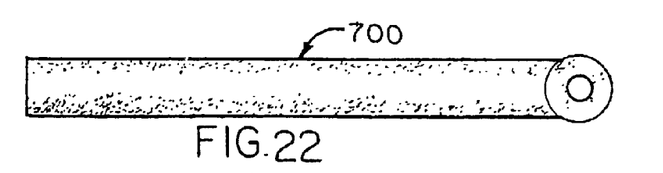
FIG. 22 is a side elevational view of another alternative embodiment of a rod of the telescoping assembly.
Figure 23:
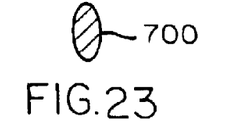
FIG. 23 is a front elevational view of the rod.
Figure 24:
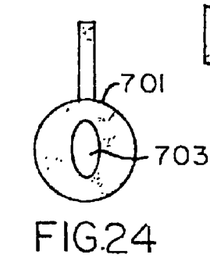
FIG. 24 is a rear elevational view of another alternative embodiment of the posterior tube.

FIGS. 22–24 illustrate another embodiment of a modified tube and rod indicated by reference numerals 700 and 701 respectively. As will be appreciated, the gross structure of the modified tube and rod are similar to those described above. However, as best seen in FIGS. 23 and 24, the rod 700 has an ovoid cross section. Tube 701 has a complementary ovoid bore 703, which is slightly oversized relative to tube 701 to allow the introduction of rod 700 into bore 703. As will be appreciated, the ovoid shapes of the bore and rod also prevent the rod from turning or rotating within the tube to retard molar tipping in use.

Figure 25:
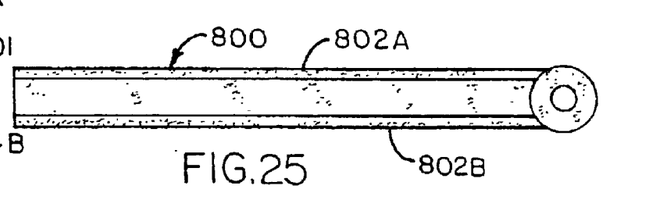
FIG. 25 is a side elevational view of yet another alternative embodiment of a rod of the telescoping assembly.
Figure 26:
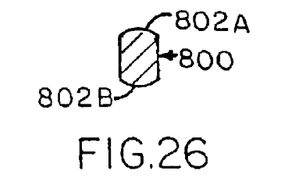
FIG. 26 is a front elevational view of the rod.
Figure 27:
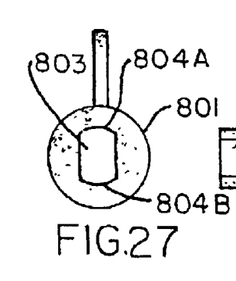
FIG. 27 is a rear elevational view of yet another alternative embodiment of the posterior tube.

FIGS. 25–27 illustrate another embodiment of the modified tube and rod indicated by reference numerals 800 and 801 respectively. As best seen in FIGS. 26 and 27, the rod 800 has a substantially rectangular cross section with rounded top and bottom outer walls 802A and 802B, respectively.

Tube 801 has a complementary substantially rectangular bore 803, having an arced or rounded top wall 804A and rounded bottom wall 804B which is slightly oversized relative to tube 601 to allow the introduction of rod 800 into bore 803. The rounded walls on the tube and rod facilitate ease of movement for adjustment; the flat side walls facilitate soldering and prevent the rod from turning or rotating within the tube to retard molar tipping.

The designs shown in FIGS. 22–27 can be employed in any of the previously described and illustrated expanders. The designs of FIGS. 22–27 can be used to replace rod 37 and tube 45 as shown in FIG. 1B. Likewise the embodiments of FIGS. 22–27 can be incorporated in the expander shown in FIG. 1D in place of rod 237 and tube 245. The designs of FIGS. 22–27 can also be used for the tube 63 and rod 61 of FIG. 1C. The present invention contemplates the use of a rod and tube assembly that resists twisting or rotation in any expander that uses a novel rod and tube assembly. It will be appreciated that the illustrated designs that resist twisting or rotation are intended to be usable in any orthodontic expander that includes at least one rod and tube assembly. It will also be appreciated that the different rod and tube assemblies in the orthodontic appliance can have different cross-sectional configurations. Stated differently, the rod and tube assemblies of the orthodontic appliance need not all have the same cross-sectional configuration. For example, all of the various rod and tube embodiments as described herein, in order to add to the safety of the appliance when applied to the mouth of the patient, may be embedded in an acrylic, or other soft plastic, to add to the appearance, attractiveness, and safety attributes, of the appliance, when applied in the patient's mouth. In addition, these rod and tube arrangements may be slightly displaced from their attachment to their shown bands, such as band 421, depending upon the convenience required for the patient being treated.

In view of the above, it will be seen that the several objects and advantages of the present invention have been achieved and other advantageous results have been obtained. Furthermore, since various changes and modifications may be made in the assemblies of the present invention without departing from the scope of the claims, the foregoing description and accompanying drawings are intended to be illustrative only and should not be construed in a limiting sense.

What is claimed is:

1. An orthodontic appliance for expanding the mandibular or maxillary arch comprising:
   a first forward orthodontic band;
   a second forward orthodontic band;
   a first spring-loaded rod and tube assembly between said first and second forward orthodontic bands;
   a first rear orthodontic band and a second rear orthodontic band;
   a second spring-loaded rod and tube assembly connecting said first forward and first rear orthodontic bands; and
   a third spring-loaded rod and tube assembly connecting said second forward and second rear orthodontic bands;
   said rod and tube assemblies each having a first tube that slidably receives a rod,
   a second tube coaxial with the rod that receives said first tube, and a spring coaxial and within said second tube; said rods and said first tubes having complementary cross-sectional shapes to avoid relative rotation.

2. The orthodontic appliance of claim 1 wherein said rods and said first tubes each have a cross-section of one of polygonal, square, and straight side walls with rounded top and bottom walls.

3. The orthodontic appliance of claim 1 wherein said rods and said first tubes each have a cross-section of one of ovoid, truncated circles, and round.

4. The orthodontic appliance of claim 1 wherein said appliance is a mandibular arch expander.

5. The orthodontic appliance of claim 1 wherein said appliance is a maxillary arch expander.

6. An orthodontic appliance for expanding and lengthening the mandibular and maxillary arch of a human patient, the appliance comprising:
   a mandibular arch expander having a pair of forward orthodontic bands, a pair of rear orthodontic bands, a first mandibular expansion assembly to expand said mandibular arch expander, and a second mandibular expansion assembly to lengthen said mandibular arch expander;
   a maxillary arch expander including a pair of forward orthodontic bands, a pair of rear orthodontic bands, and a maxillary expansion assembly to expand said maxillary arch expander; and
   a telescoping assembly extending between and connecting said mandibular and maxillary arch expanders; said telescoping assembly having a first end and a second end; said first end of said telescoping assembly being operatively connected to one of said forward and rear bands of said mandibular arch expander and the second end of said telescoping assembly being operatively connected to the other of said forward and rear bands of said maxillary arch expander; the telescoping assembly including a first tube, a rod slidably received in the first tube, and a second tube coaxial with the rod that receives said first tube, said telescoping assembly being adjustable to lengthen the assembly when installed within the mouth of a patient, without resort to removing the rod from the first tube; said rod and said first tube having complementary cross-sectional shapes to avoid relative rotation.

7. The orthodontic appliance of claim 6 wherein said rods and said first tubes each have a cross-section of one of polygonal, square, and straight side walls with rounded top and bottom walls.

8. The orthodontic appliance of claim 6 wherein said rods and said first tubes each have a cross-section of one of ovoid, truncated circles, and round.

9. An orthodontic appliance for expanding and lengthening the mandibular and maxillary arch of a human patient, the appliance comprising:
   a mandibular arch expander having a pair of forward orthodontic bands, a pair of rear orthodontic bands;
   a maxillary arch expander including a pair of forward orthodontic bands, a pair of rear orthodontic bands;
   a pair of adjustable connector assemblies; said connector assemblies each comprising an expandable tube assembly and a rod which extends through said expandable tube assembly; said expandable tube assembly having a mount at a first end thereof adapted to connect said tube assembly to said rear orthodontic band of said maxillary arch; said rod having a mount adjacent a second end of said expandable tube assembly adapted to be connected to said front orthodontic bands of said mandibular arch expander;
   the tube assembly including a hollow posterior tube and an anterior tube which is telescopically connected, said anterior tube includes a hollow body having an exter nally threaded back end and said posterior tube includes a hollow body defining a bore, said posterior tube being internally threaded at a front end of said tube, said posterior tube bore being sized to accept said anterior tube, said posterior and anterior tubes being threadedly connected together;

said anterior tube defining a channel; said rod and said channel having complementary cross-sectional shapes to avoid relative rotation.

10. The orthodontic appliance of claim 9 said rods and said channels each have a cross-section of one of polygonal, square, and straight side walls with rounded top and bottom walls.

11. The orthodontic appliance of claim 9 wherein said rods and said channels each have a cross-section of one of ovoid truncated circles, and round.

* * * * *